(12) United States Patent
Dwivedi et al.

(10) Patent No.: US 9,034,901 B2
(45) Date of Patent: May 19, 2015

(54) PITAVASTATIN CALCIUM AND PROCESS FOR ITS PREPARATION

(75) Inventors: Shriprakash Dhar Dwivedi, Ahmedabad (IN); Dhimant Jasubhai Patel, Ahmedabad (IN); Alpesh Pravinchandra Shah, Ahmedabad (IN); Brij Khera, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 13/818,681

(22) PCT Filed: Aug. 24, 2011

(86) PCT No.: PCT/IN2011/000571
§ 371 (c)(1),
(2), (4) Date: May 8, 2013

(87) PCT Pub. No.: WO2012/025939
PCT Pub. Date: Mar. 1, 2012

(65) Prior Publication Data
US 2014/0148481 A1 May 29, 2014

(30) Foreign Application Priority Data
Aug. 25, 2010 (IN) .......................... 2374/MUM/2010

(51) Int. Cl.
*C07D 215/14* (2006.01)
(52) U.S. Cl.
CPC .................................. *C07D 215/14* (2013.01)

(58) Field of Classification Search
None
See application file for complete search history.

(56) References Cited

U.S. PATENT DOCUMENTS

| | | |
|---|---|---|
| 2004/0249154 A1 | 12/2004 | Chen |
| 2009/0176987 A1 | 7/2009 | Ohara et al. |
| 2009/0182008 A1 | 7/2009 | Van Der Schaaf |

FOREIGN PATENT DOCUMENTS

| | | |
|---|---|---|
| CN | 101195603 A | 6/2008 |
| WO | 2010077062 A2 | 7/2010 |

OTHER PUBLICATIONS

Manne Satyanarayana Reddy et al; "An Improved Industrial Process for Synthesis of HMG-CoA Reductase Inhibitor Pitavastation," Oriental Journal of Chemistry, IQBAL, Phopal, IN., vol. 23, No. 2, Jan. 1, 2007, pp. 559-564.
European Patent Office Acting as The International Search Authority, International Search Report, PCT/IN2011/000571, Oct. 27, 2011.
European Patent Office Acting as The International Preliminary Examining Authority, International Preliminary Report on Patentability, PCT/IN2011/000571, Jan. 19, 2012.

*Primary Examiner* — Timothy R Rozof
(74) *Attorney, Agent, or Firm* — Brij Khera; William D. Hare; McNeely, Hare & War, LLP (57) ABSTRACT

The invention provides the process for the preparation of pitavastatin and its pharmaceutically acceptable salts thereof. In particular, the invention provides a process for the preparation of stable pitavastatin calcium in crystalline form having water content less than 5% wt/wt. The present invention also provides stable crystalline form of pitavastatin calcium substantially free from crystal Form-A and use thereof for pharmaceutical compositions.

32 Claims, 5 Drawing Sheets

PITAVASTATIN CALCIUM AND PROCESS FOR ITS PREPARATION

FIELD OF THE INVENTION

The invention relates to processes for the preparation of pitavastatin and its pharmaceutically acceptable salts thereof. In particular, the invention relates to a process for the preparation of stable pitavastatin calcium in crystalline form having water content less than 5% wt/wt. More particularly, the present invention relates to a stable crystalline form of pitavastatin calcium substantially free from crystal Form-A. The invention also relates to crystalline pitavastatin calcium and pharmaceutical compositions that include the crystalline pitavastatin calcium.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Pitavastatin calcium is chemically known as (3R,5S)-7-[2-cyclopropyl-4-(4-flourophenyl)-quinolin-3-yl]-3,5-dihydroxy-6-(E)-heptenoic acid calcium salt having the Formula I is known in the literature.

(I)

Pitavastatin is a synthetic lipid-lowering agent that acts as an inhibitor of 3-hydroxy-3-methylglutaryl-coenzyme a (HMG-CoA) reductase (HMG-CoA Reductase inhibitor). This enzyme catalyzes the conversions of HMG-CoA to mevalonate, inhibitors are commonly referred to as "statins". Statins are therapeutically effective drugs used for reducing low density lipoprotein (LDL) particle concentration in the blood stream of patients at risk for cardiovascular disease. Pitavastatin is used in the treatment of hyperchloesterolemia and mixed dyslipidemia.

Pitavastatin calcium has recently been developed as a new chemically synthesized and powerful statin by Kowa Company Ltd, Japan. On the basis of reported data, the potency of pitavastatin is dose-dependent and appears to be equivalent to that of atorvastatin. This new statin is safe and well tolerated in the treatment of patients with hypercholesterolaemia.

Significant interactions with a number of other commonly used drugs can be considered to be extremely low.

Processes for the preparation of pitavastatin are described in EP-A-0304063 and EP-A-1099694 and in the publications by N. Miyachi et al. in *Tetrahedron Letters* (1993) vol. 34, pages 8267-8270 and by K. Takahashi et al. in *Bull. Chem. Soc. Japan* (1995) Vol. 68, 2649-2656. These publications describe the synthesis of pitavastatin in great detail but do not describe the hemi-calcium salt of pitavastatin. The publications by LA. Sorbera et al. in *Drugs of the Future* (1998) vol. 23, pages 847-859 and by M. Suzuki at al. in *Bioorganic & Medicinal Chemistry Letters* (1999) vol. 9, pages 2977-2982 describe pitavastatin calcium, however, a precise procedure for its preparation is not given. A full synthetic procedure for the preparation of pitavastatin calcium is described in EP-A-0520406. In the process described in this patent, pitavastatin calcium is obtained by precipitation from an aqueous solution as a white crystalline material with a melting point of 190-192° C.

US 2009/0182008 A1 discloses various polymorphic forms A, B, C, D, E, and F, and the amorphous form of pitavastatin calcium salt (2:1). In particular, the crystalline Form A having water content from about 5% to about 15% and process for its preparation are disclosed.

US 2009/0176987 A1 ("the US '987 A1) also discloses polymorphic form crystal form A of pitavastatin calcium which contains from 5 to 15% of water and which shows, in its X-ray powder diffraction as measured by using CuKα radiation, a peak having a relative intensity of more than 25% at a diffraction angle (2θ) of 30.16°.

The US '987 A1 discloses that pitavastatin calcium (Crystal Form-A) when subjected to drying in a usual manner, the crystallinity decreases to a state which is close to an amorphous state and is shown by X-ray powder diffraction pattern as shown in FIG. 2 when the water content becomes about 4%. It is also disclosed that even the crystallinity decreases close to an amorphous state for compound having X-ray powder diffraction pattern as shown in FIG. 1 prior to the drying. It is also disclosed that the stability of crystal Form-A and crystallinity has a very close relationship with respect to water content. Further, it has been reported that the pitavastatin calcium, which has become amorphous, has very poor stability during the storage, as shown in Table. 1.

Table.1 of the US '987 A1 also shows that pitavastatin calcium kept at 40° C. (air tight) has water content of about 7.89 (initial) and 7.81 (after 90 days) with total impurities 0.179 (initial) and 0.211 (after 90 days) with purity of 99.38% (Initial) and 99.64 (after 90 days). Contradictorily, it shows reports that pitavastatin calcium kept in open air has water content of about 7.89 (initial) and 1.77 (after 90 days) with total impurities 0.179 (initial) and 2.099 (after 90 days) with purity of 99.38% (Initial) and 96.49 (after 90 days).

The US '987 A1 also discloses that stability of pitavastatin calcium can be remarkably improved by controlling the water content in the drug substance within a specific range. Also, it reports that there are three types of crystal forms having the same water content range i.e. Crystal Form-A, Crystal Form-B and Crystal Form-C. It has been found that among the three crystalline forms, crystal Form-A is most preferred as a drug substance for pharmaceuticals.

Crystal Form-A is having water content in the range of 5% to 15%, preferably from 9% to 11%. It also discloses that Crystal Form-A is the best as a drug substance for pharmaceuticals.

International (PCT) Publication No. WO 2007/132482 A1 discloses a process for the preparation of pitavastatin calcium by condensing bromide salt of Formula-3 with aldehyde compound of Formula-4 to obtain olefinic compound of Formula-5 and converting olefinic compound to pitavastatin calcium via organic amine salt for purification.

International (PCT) Publication No. WO 2010/089770 A2 discloses a process for the preparation of pitavastatin calcium. WO 2011/089623 A2 discloses alkali or alkaline earth metal salts of pitavastatin.

Polymorphism is defined as the ability of a substance to crystallize in more than one crystal lattice arrangement. Polymorphism can influence many aspects of solid state properties of a drug. Different crystal modifications of a substance may differ considerably from one another in many respects such as their solubility, dissolution rate and finally bioavailability. An exhaustive treatment of polymorphism in pharmaceutical and molecular crystals is given e.g. by Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Decker, Inc., New York, Basel, 1999) or Bernstein (Bernstein, J., "Polymorphism in Molecular Crystals", Oxford University Press, 2002).

In view of the above, it is therefore, desirable to provide an efficient more economical, less hazardous and eco-friendly process for the preparation of highly pure stable pitavastatin calcium having water content less than 5% wt/wt. The crystalline form provided herein is at least stable under ordinary stability conditions with respect to purity, storage and is free flowing powder. The process is simple, cost-effective, eco-friendly and commercially viable.

SUMMARY OF THE INVENTION

In one general aspect there is provided storage stable pitavastatin calcium in crystalline form having water content less than about 5% wt/wt.

In another general aspect there is provided a stable pitavastatin calcium in crystalline form characterized by X-ray powder diffraction peaks at about 6.7°, 9.0°, 11.1°, 19.6°, 21.0°±0.2° (2θ) and having water content less than about 5% wt/wt.

In another general aspect there is provided a stable pitavastatin calcium which is substantially free from crystal Form-A and doesn't show an X-ray powder diffraction peak having relative intensity of more than 25% at a diffraction angle (2θ) of 30.16°. In another general aspect there is provided a process for the preparation of a stable crystalline form of pitavastatin calcium having water content less than about 5% wt/wt, the process comprising:
a) obtaining a solution of pitavastatin calcium in one or more solvents; and
b) isolating the crystalline pitavastatin calcium optionally, in presence of one or more anti-oxidants.

In further aspect, there is provided a process for the preparation of stable pitavastatin calcium of Formula I (I)

having water content less than 5% wt/wt and characteristic peak in X-ray powder diffraction at about 6.7°, 9.0°, 11.1°, 19.6°, 21.0°±0.2° (2θ)
the process comprising:
(a) reacting the phosphonium bromide compound of Formula-IV with an aldehyde compound of Formula-III in presence of an alkali or alkaline earth metal bases in one or more of suitable solvent to provide an olefin compound of Formula-II,
(b) hydrolyzing the olefinic compound of Formula-II by subjecting under the acidic conditions to remove the acetonide and form diol compound, which upon treating with an alkali metal hydroxide base to form the corresponding alkali metal salt of pitavastatin (Ia);
(c) treating alkali metal salt of pitavastatin with a calcium source to obtain pitavastatin calcium (I);
(d) obtaining a solution of pitavastatin calcium in one or more solvents; and
(e) isolating the crystalline pitavastatin calcium optionally, in the presence of one or more anti-oxidants.

According to the further aspect, there is provided a process for the preparation of pitavastatin calcium in stable crystalline form having water content less than about 5% wt/wt,
the process comprising:
(a) providing pitavastatin calcium in crystalline form having water content in the range of 8% to 12%;
(b) contacting pitavastatin calcium with humid air in a fluidized bed drier, or maintaining the pitavastatin calcium at a temperature of from about 5° to about 60° C., under pressure of less than 30 mm/Hg for a period of from about 1 to 5 days;
(c) recovering pitavastatin calcium in crystalline form having water content less than 5% wt/wt; and
(d) stabilizing crystalline pitavastatin calcium by packing under controlled condition.

In further aspect, there is provides a process for stabilizing crystalline pitavastatin calcium having water content less than about 5% wt/wt and characteristic peak in X-ray powder diffraction at about 6.7°, 9.0°, 11.1°, 19.6°, 21.0°±0.2° (2θ),
the process comprising:
(a) placing crystalline pitavastatin calcium under nitrogen atmosphere in a double polythene bag or non-permeable bag tied with a thread;
(b) placing the bag of step (a) inside a black color polyethylene bag, optionally containing oxygen busters and sealing it;
(c) placing the bag of step (b) inside a triple laminated bag, optionally containing oxygen busters and sealing it; and
(d) placing the sealed triple laminated bag inside a high density polyethylene (HDPE) container, sealing it and storing in a controlled environment chamber from about 25° C. to about 40° C.

According to the further aspect, there is provided substantially pure pitavastatin calcium in stable crystalline form.

In another aspect, the present invention accordingly provides a pharmaceutical composition comprising a therapeutically effective amount of crystalline pitavastatin calcium having water content of less than about 5% and one or more pharmaceutically acceptable carriers, excipients or diluents.

An aspect of the present application provides A pharmaceutical composition comprising a therapeutically effective amount of crystalline pitavastatin calcium having water content less than about 5% and substantially free from one or more of its corresponding impurities as measured by HPLC.

DETAILED DESCRIPTION OF THE DRAWINGS

DETAILED DESCRIPTION ON THE INVENTION

The prior art discloses the use of organic amine salts of pitavastatin for obtaining better purity. The present inventors have found that pitavastatin calcium prepared by using the process provided herein provides better yield and purity and avoids the use of amine salt formation. This significantly improves the process economics and commercial viability.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggest otherwise.

As used here in the term "isolation" may include filtration, filtration under vacuum, centrifugation, and decantation. The product obtained may be further or additionally dried to achieve the desired moisture values. For example, the product may be dried in a tray drier, dried under vacuum and/or in a Fluid Bed Drier.

All ranges recited herein include the endpoints, including those that recite a range "between" two values. Terms such as "about", "general", "substantially" and the like are to be construed as modifying a term or value such that it is not an absolute. Such terms will be defined by the circumstances and the terms that they modify as those terms are understood by those skill in the art. This includes, at very least, the degree of expected experimental error, technique error and instrument error for a given technique used to measure a value.

The term "substantially pure" means stable pitavastatin calcium containing less than about 0.15% (wt/wt) any single individual impurities like desflouro impurity, cis-isomer impurity, pitavastatin 5-oxo impurity, pitavastatin Lactone impurity, pitavastatin t-butyl diol ester impurity, and pitavastatin condensed by area percentage of HPLC or containing less than about 0.3% (wt/wt) pitavastatin diastereomeric impurity and pitavastatin enantiomeric impurity.

The term "controlled conditions" refers to packing under nitrogen atmosphere and in a double polythene bag or non-permeable bag tied with a thread, keeping primary packing containing crystalline pitavastatin calcium inside a black color polyethylene bag optionally containing oxygen busters and sealing it, placing above the double polyethylene bag or non-permeable bag inside a triple laminated bag optionally containing oxygen busters and sealing it, and placing the sealed triple laminated bag inside a closed high density polyethylene (HDPE) container and storing in controlled environment chamber at about 25° C. to about 40° C.

The term "suitable solvent" means a single or a combination of two or more solvents.

In one general aspect, there is provided storage stable pitavastatin calcium in crystalline form having water content less than about 5% wt/wt.

Figure 1:
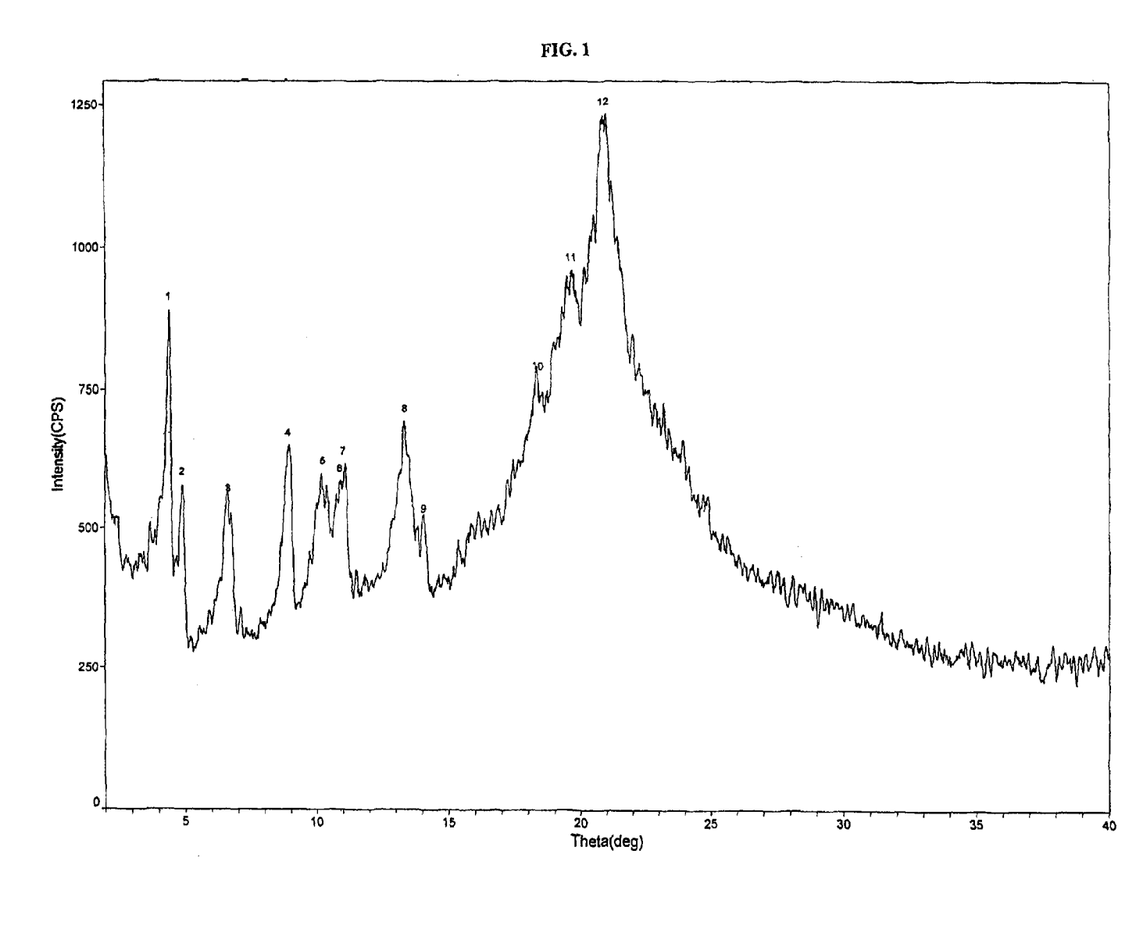
FIG. 1: X-ray diffraction pattern of crystalline pitavastatin calcium as per process of present invention.
Figure 2:
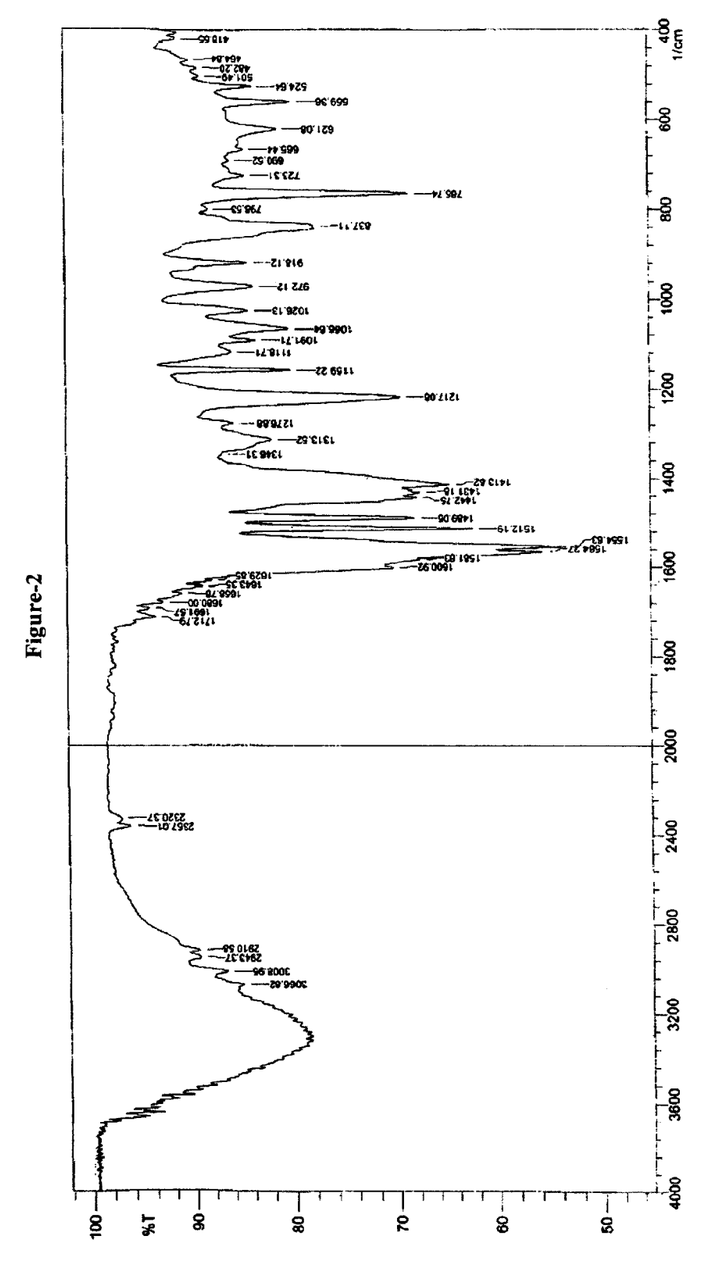
FIG. 2: IR spectra of crystalline pitavastatin calcium as per process of present invention.
Figure 3:
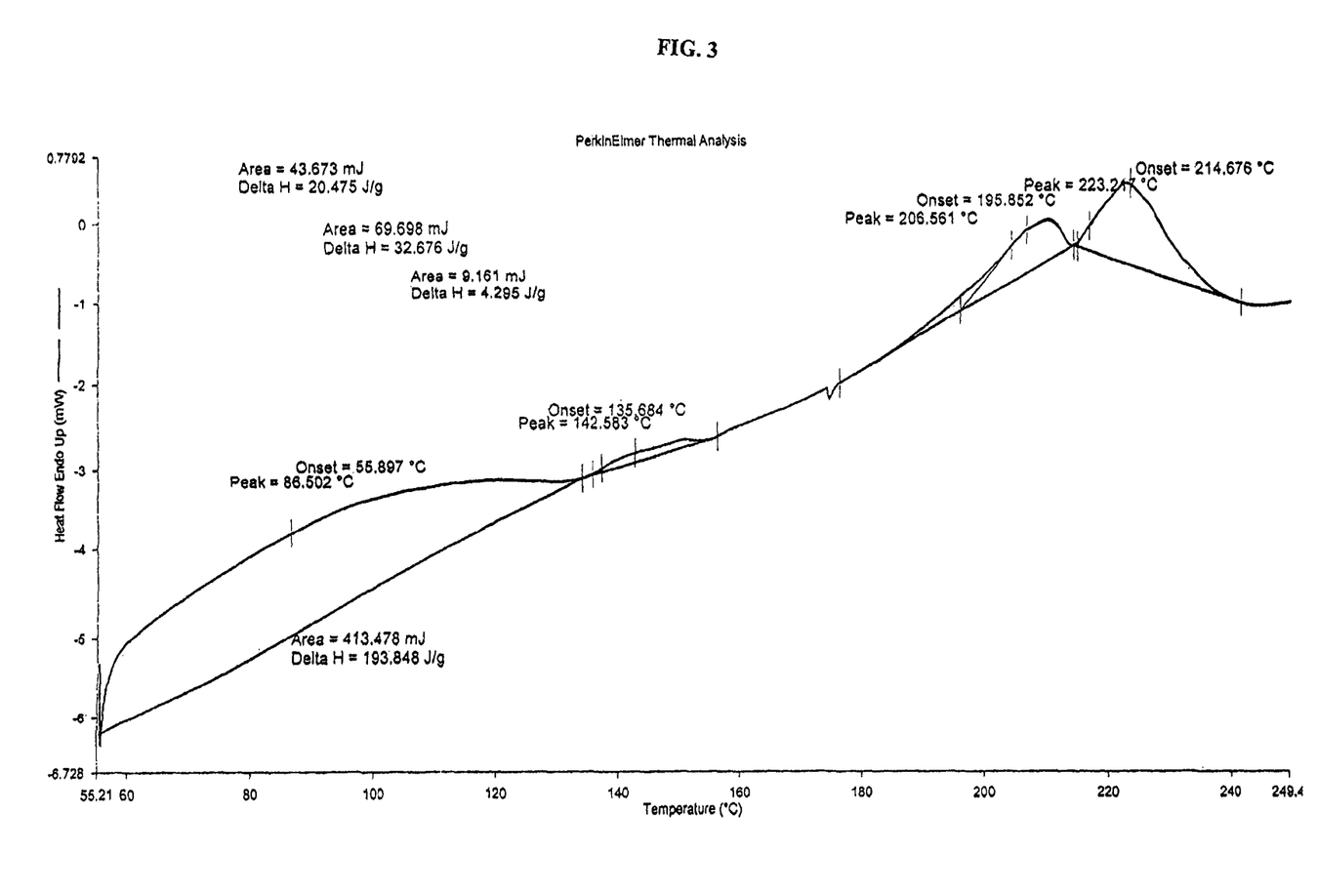
FIG. 3: Differential Scanning Calorimetry analysis of crystalline pitavastatin calcium as per process of present invention.
Figure 4:
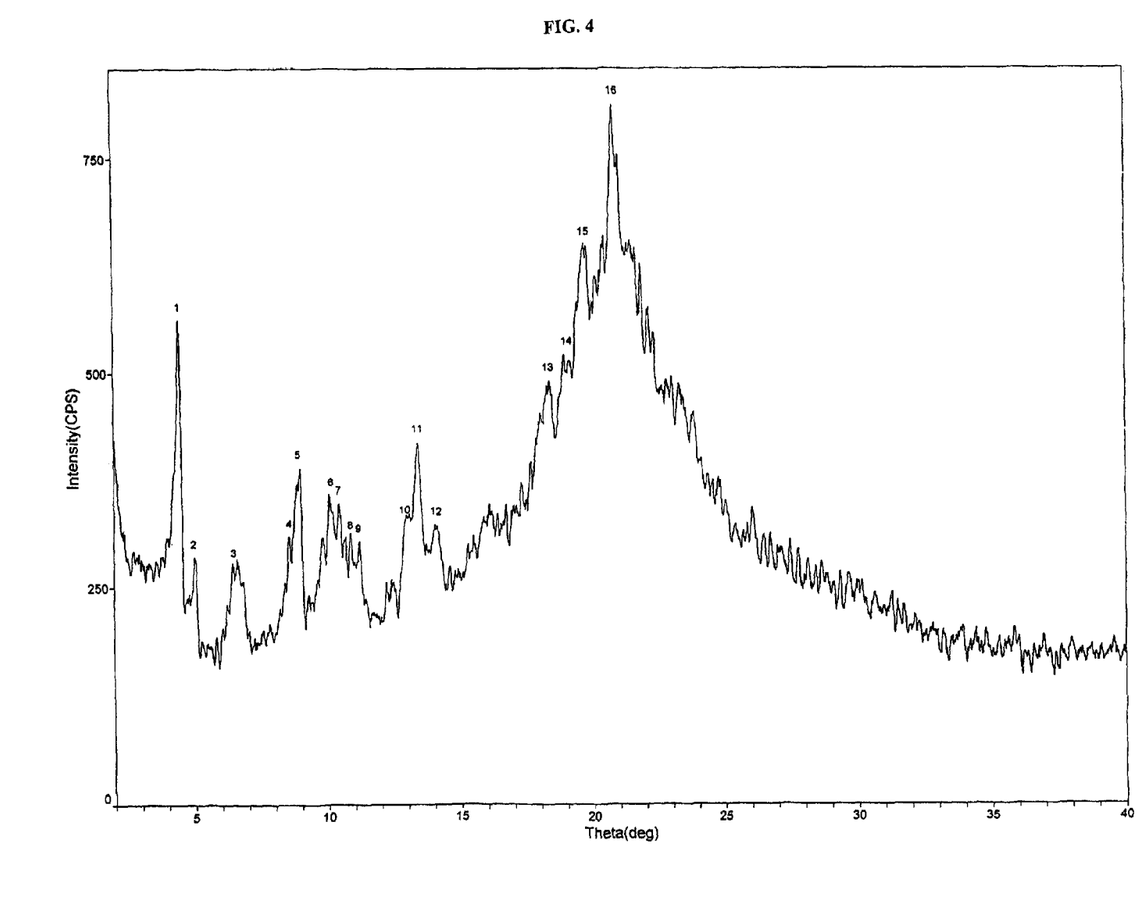
FIG. 4: X-ray diffraction pattern of stable crystalline pitavastatin calcium after exposure to a relative humidity of 75% at 40° C. for a period of at least three months.
Figure 5:
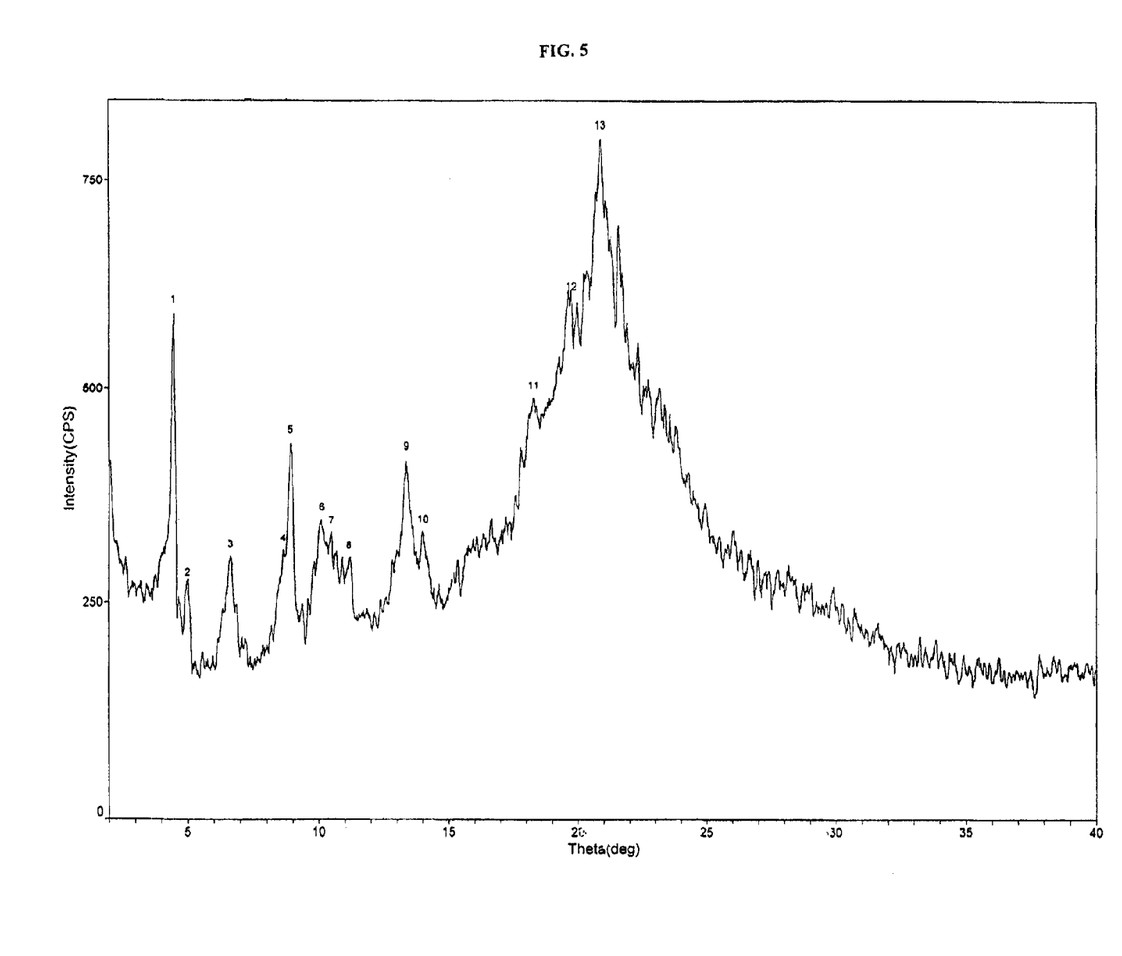
FIG. 5: X-ray diffraction pattern of stable crystalline pitavastatin calcium after exposure to a relative humidity of 60% at 25° C. for a period of at least three months.

In another general aspect, there is provided stable pitavastatin calcium in crystalline form characterized by X-ray powder diffraction peaks at about 6.7°, 9.0°, 11.1°, 19.6°, 21.0°±0.2° (2θ) and having X-ray powder diffraction pattern as shown in FIG. 1.

According to an aspect, the present invention provides stable pitavastatin calcium (1), which is substantially free from crystal Form-A characterized by X-ray powder diffraction having a peak of relative intensity of more than 25% at a diffraction angle (2θ) of 30.16°.

Herein the term "substantially free from crystal Form-A" means less than about 1%, particularly less than 0.1%, more particularly not in detectable amount of crystal Form-A, as appropriate or in the case of crystalline solids.

As used herein, "stable pitavastatin calcium" includes either of the following:

(a) pitavastatin calcium is substantially free from crystal Form-A and doesn't show an X-ray powder diffraction peak having relative intensity of more than 25% at a diffraction angle (2θ) of 30.16° after storage for 3 months at 40° C. and a relative humidity of 75%, or (b) pitavastatin calcium is substantially free from crystal Form-A and doesn't show an X-ray powder diffraction peak having relative intensity of more than 25% at a diffraction angle (2θ) of 30.16° after storage for 3 months at 25° C. and a relative humidity of 60%, or (c) pitavastatin calcium containing less than about 0.15% (wt/wt) any single individual impurities like desflouro impurity, cis-isomer impurity, pitavastatin 5-oxo impurity, pitavastatin lactone impurity, pitavastatin t-butyl diol ester impurity, and pitavastatin condensed by area percentage of HPLC after storage for 3 months at 40° C. and a relative humidity of 75%, or

(d) pitavastatin calcium containing less than about 0.15% (wt/wt) any single individual impurities like desflouro impurity, cis-isomer impurity, pitavastatin 5-oxo impurity, pitavastatin lactone impurity, pitavastatin t-butyl diol ester impurity, and pitavastatin condensed by area percentage of HPLC after storage for 3 months at 25° C. and a relative humidity of 60%, or (e) crystalline pitavastatin calcium that after exposure to a relative humidity of 75% at 40° C. for a period of at least three months does not have water content greater than 5% wt/wt, or (f) crystalline pitavastatin calcium that after exposure to a relative humidity of 75% at 40° C. for a period of at least three months does not show a peak having a relative intensity of more than 25% at a diffraction angle (2θ) of 30.16°.

The above impurities are present in the preparation of pitavastatin calcium includes the following which were determined from an HPLC analysis of different batches of pitavastatin calcium produced by the process described in the specification herein after, and identified below in the scheme-1.

Scheme-1

Des-Flouro Pitavastatin

Pitavastatin 5-oxo Impurity

Pitavastatin Lactone Impurity

Pitavastatin t-butyl diol ester Impurity

-continued

Pitavastatin Condensed Impurity

Pitavastatin Diastereomer Impurity

Pitavastatin Enantiomeric Impurity

In general, the stability of pitavastatin calcium crystalline form having water content 5% wt/wt at 40° C./75% RH and 25° C./60% RH is shown in Table-1.

TABLE 1

| Sr. No. | Conditions of Stability | Initial | 1 month 40° C. ± 2° C. RH 75% ± 5% | 2 month 40° C. ± 2° C. RH 75% ± 5% | 3 month 40° C. ± 2° C. RH 75% ± 5% | 3 month 25° C. ± 2° C. RH 60% ± 5% |
|---|---|---|---|---|---|---|
| 1 | Water by KF (% w/w) | 3.0 | 2.9 | 4.3 | 4.2 | 3.9 |
| 2 | Related Substances | | | | | |
| | Desflouro | 0.05 | 0.05 | 0.05 | 0.05 | 0.05 |
| | Diastereomer | 0.17 | 0.11 | 0.11 | 0.11 | 0.12 |
| | 5-oxo | 0.07 | 0.11 | 0.15 | 0.14 | 0.12 |
| | Lactone | ND | ND | ND | 0.09 | 0.07 |

TABLE 1-continued

| Sr. No. | Conditions of Stability | Initial | 1 month 40° C. ± 2° C. RH 75% ± 5% | 2 month 40° C. ± 2° C. RH 75% ± 5% | 3 month 40° C. ± 2° C. RH 75% ± 5% | 3 month 25° C. ± 2° C. RH 60% ± 5% |
|---|---|---|---|---|---|---|
| | Tert-butyl diol ester | ND | ND | ND | ND | ND |
| | Condensed | ND | ND | ND | ND | ND |
| | Single Individual | ND | ND | ND | ND | ND |
| | Total Impurities | 0.32 | 0.28 | 0.31 | 0.39 | 0.36 |

In another general aspect, there is provided a process for preparation of a stable crystalline form of pitavastatin calcium having water content less than about 5% wt/wt, the process comprising:
a) obtaining a solution of pitavastatin calcium in one or more solvents; and
b) isolating the crystalline pitavastatin calcium optionally, in the presence of one or more anti-oxidants.

In general, the solvent comprises one or more of chlorinated hydrocarbons, alcohols, ketones, aliphatic or cyclic ethers, water, or mixtures thereof. The solvent further comprises one or more of methylene dichloride, ethylene dichloride, chlorobenzene, methanol, ethanol, isopropanol, butanol, acetone, methylethyl ketone, diisopropyl ether, methyl tert-butyl ether, 1,4-dioxane, tetrahydrofuran and water, or mixtures thereof.

According to the embodiments, the anti-oxidants comprises one or more of butylated hydroxy toluene (BHT), butylated hydroxy anisole (BHA), n-propyl gallant, L-ascorbic acid or α-tocopherol.

Embodiments of the process comprising additional drying of the pitavastatin calcium obtained. The obtained pitavastatin calcium is dried till water content is less than about 5% wt/wt. The further aspect of the process includes packaging the pitavastatin calcium under controlled conditions.

According to still another aspect, the present invention provides a process for the preparation of pitavastatin calcium in stable crystalline form having water content less than about 5% wt/wt, the process comprising:
(a) providing pitavastatin calcium in crystalline form having water content in the range of 8% to 12%;
(b) contacting pitavastatin calcium with humid air in a fluidized bed drier;
(c) maintaining the pitavastatin calcium at a temperature of from about 5 to about 60° C., under pressure of less than 30 mm/Hg for a period of from about 1 hour to about 5 days; and
(d) recovering the pitavastatin calcium in crystalline form having water content less than about 5% wt/wt.

According to one embodiment, the invention present invention provide a process for stabilizing crystalline pitavastatin calcium having water content less than about 5% wt/wt and characteristic peak in X-ray powder diffraction at about 6.7°, 9.0°, 11.1°, 19.6°, 21.0°±0.2° (2θ), the process comprising:
(a) placing crystalline pitavastatin calcium under nitrogen atmosphere in a double polythene bag or non-permeable bag tied with a thread;
(b) placing the bag of step (a) inside a black color polyethylene bag, optionally containing oxygen busters and sealing it;
(c) placing the bag of step (b) inside a triple laminated bag, optionally containing oxygen busters and sealing it; and
(d) placing the sealed triple laminated bag inside a high density polyethylene (HDPE) container, sealing it and storing in a controlled environment chamber from about 25° C. to about 40° C.

In further general aspect, there is provided a process for the preparation of stable pitavastatin calcium of Formula I (I)

having water content less than about 5% wt/wt and characteristic peak in X-ray powder diffraction at about 6.7°, 9.0°, 11.1°, 19.6°, 21.0°±0.2° (2θ), the process comprising:
(a) reacting the phosphonium bromide compound of Formula-IV (IV)

with an aldehyde compound of Formula-III in presence of an alkali or alkaline earth metal bases in one or more of suitable solvent to provide an olefin compound of Formula-II, (b) hydrolyzing the olefinic compound of Formula-II by subjecting under the acidic conditions to remove the acetonide and form diol compound, which upon treating with an alkali metal hydroxide base to form the corresponding alkali metal salt of pitavastatin (Ia);

(c) treating the alkali metal salt of pitavastatin (Ia) with a calcium source to obtain pitavastatin calcium (I);
(d) obtaining a solution of pitavastatin calcium in one or more solvents; and
(e) isolating the crystalline pitavastatin calcium optionally, in the presence of one or more anti-oxidants.

In general, the phosphonium bromide compound of Formula-IV and aldehyde compound of Formula-III can be reacted in presence of alkali or alkaline earth metal bases. The alkali or alkaline earth metal bases comprises of one or more of sodium hydroxide, potassium hydroxide, lithium hydroxide, potassium carbonate, sodium carbonate, lithium carbonate, cesium carbonate and the like, particularly potassium carbonate.

Embodiments includes reaction in suitable solvent comprises one or more of dimethylformamide, dimethylsulfoxide, dimethylacetamide, tetrahydrofuran, N-methylpyrrolidone or mixtures thereof, particularly dimethylsulfoxide.

The reaction is at an ambient temperature i.e. at about 15° C. to about 40° C., preferably from about 20° C. to about 35° C. The reaction mixture can be stirred for about 5 to 15 hours till completion of the reaction, preferably for 10 hours. The reaction mixture can be further treated with non-polar solvents like toluene, xylene, methylene dichloride, ethyl acetate for extracting olefin compound of Formula-II, preferably toluene.

The olefin compound of Formula-II can be isolated by removal of toluene followed by addition of isopropanol. After the addition of isopropanol, the reaction mixture can be heated to 40° C. to 80° C., preferably 60° C. to 70° C. and cooling to 15° C. to obtain olefin compound of Formula (II). The compound of Formula (II) can be purified in suitable polar solvent selected from one or more of methanol, ethanol, Isopropanol, acetone, dimethylformamide and the like, particularly methanol.

Further embodiments of the process includes, hydrolysis of olefin compound of Formula (II). The hydrolysis of olefin compound is done by subjecting under the acidic conditions to remove the acetonide and form diol compound. The suitable acid comprises one or more of hydrochloric acid, acetic acid, sulfuric acid, nitric acid, phosphoric acid and the like. In particular, the hydrochloric acid can be used.

The diol compound obtained in-situ is treated with alkali metal hydroxide comprises one or more of sodium hydroxide, potassium hydroxide, lithium hydroxide and the like. In particular, sodium hydroxide can be used to obtain corresponding alkali metal salt of pitavastatin (Ia)

herein M is $Na^+$.

Embodiments of the process include treating alkali metal salt of Formula (Ia) of pitavastatin, preferably pitavastatin sodium with calcium source. The preferred calcium source comprises one or more of calcium chloride, calcium methoxide, calcium acetate and hydrates thereof. In particular, calcium chloride hexahydrate can be used as calcium source.

In general, the solvent in step (d) comprises one or more of chlorinated hydrocarbons, alcohols, ketones, aliphatic or cyclic ethers, water, or mixtures thereof. Particularly, the solvent comprises one or more of methylene dichloride, ethylene dichloride, chlorobenzene, methanol, ethanol, isopropanol, butanol, acetone, methylethyl ketone, diisopropyl ether, methyl tert-butyl ether, 1,4-dioxane, tetrahydrofuran and water, or mixtures thereof.

The suitable anti-oxidant comprises of one or more of butylated hydroxy toluene, butylated hydroxy anisole, n-propyl gallant, L-ascorbic acid or α-tocopherol, preferably, butylated hydroxy anisole.

In general, the pitavastatin calcium prepared by the process as described above, can be dried under vacuum in hot air oven at 60° C. to 65° C. for about 1 to 5 hours to obtain pitavastatin calcium having water content limit in the range of 2.0 to 4.0%. Hence, it is also the scope of the present invention, to dry pitavastatin calcium till constant weight of less than 5% to provide stable pitavastatin calcium.

Embodiments includes drying pitavastatin calcium containing about 8% to 12% water content by Karl Fisher method for about 1 hour to about 5 hours, particularly at least about 1 hour so as obtain less than 5% wt/wt of water content to provide stable pitavastatin calcium.

According to the further embodiments, there is provided a process for the preparation of pitavastatin calcium in crystalline form having water content less than about 5% wt/wt and characteristic peak in X-ray powder diffraction at about 6.7°, 9.0°, 11.1°, 19.6°, 21.0°±0.2° (2θ), the process comprising:
(a) providing a solution comprising pitavastatin calcium (I) in a suitable organic solvent wherein the organic solvent is selected from one or more of chlorinated solvent, alcoholic solvent, ketonic solvent, aliphatic or cyclic ether and mixtures thereof;
(b) adding suitable antisolvent and mixture thereof to the solution; and
(c) recovering the crystalline form of pitavastatin calcium optionally in presence of anti-oxidants;
(d) drying crystalline pitavastatin calcium till water content is less than about 5% wt/wt; and
(b) stabilizing crystalline pitavastatin calcium by packing under controlled condition.

The process for preparation of crystalline pitavastatin calcium includes, addition of anti-solvent to a concentrated solution of pitavastatin calcium in an organic solvent.

Embodiments of the process includes preparing the solution of pitavastatin calcium in suitable organic solvent selected from one or more of chlorinated solvent, alcoholic solvent, ketonic solvent, aliphatic or cyclic ether and mixtures thereof. The preferred solvent can be selected from one or more of methylene dichloride, ethylene dichloride, chlorobenzene, methanol, ethanol, isopropanol, butanol, acetone, methylethyl ketone, diisopropyl ether, methyl tert-butyl ether, 1,4-dioxane, tetrahydrofuran and water or mixtures thereof. In particular, acetone or tetrahydrofuran.

In general, the embodiments of the process include adding suitable antisolvent to the solution of pitavastatin calcium in suitable organic solvent. The suitable anti-solvent can be selected from one or more of hexane, heptane, cyclohexane, toluene, xylene, ethyl acetate and the like. In particular, heptane or cyclohexane.

It is preferable that the anti-solvent and solvent are miscible. The crystalline form can be prepared by further drying and stabilization to obtain stable pitavastatin calcium by removal of solvent from the solution of Pitavastatin Calcium in a suitable solvent.

In another preferred feature, the anti-oxidant is selected from the group consisting of butylated hydroxy toluene, butylated hydroxy anisole, n-propyl gallant, L-ascorbic acid or a-tocopherol. In particular, butylated hydroxy toluene (BHT) or butylated hydroxy anisole (BHA).

According to the further embodiment, there is provided substantially pure pitavastatin calcium in stable crystalline form.

In another aspect, the present invention provides a pharmaceutical composition comprising a therapeutically effective amount of crystalline pitavastatin calcium having water content less than about 5% and substantially free from one or more of its corresponding impurities as measured by HPLC.

The impurities as measured by HPLC comprises one or more of desflouro impurity, cis-isomer impurity, pitavastatin 5-oxo impurity, pitavastatin lactone impurity, pitavastatin t-butyl diol ester impurity and pitavastatin condensed impurity when measured by area percentage of HPLC. Further, the aspect also includes impurities like pitavastatin enantiomeric impurity and pitavastatin diastereoisomer impurity.

In another aspect, the present invention accordingly provides a pharmaceutical composition comprising a therapeutically effective amount of crystalline pitavastatin calcium having water content of less than about 5% and one or more pharmaceutically acceptable carriers, excipients or diluents.

In another aspect, the present invention accordingly provides a pharmaceutical composition comprising crystalline pitavastatin calcium having water content of less than 5% substantially free of crystal Form A having a peak of relative intensity of more than 25% at a diffraction angle (2θ) of 30.16°.

In an aspect of the present application, there is provided crystalline pitavastatin calcium characterized by X-ray powder diffraction peaks at about 6.7°, 9.0°, 11.1°, 19.6°, 21.0°±0.2° (2θ) having a particle size distribution wherein the $10^{th}$ volume percentile particle size ($D_{10}$) is less than about 20 μm, the 50th volume percentile particle size ($D_{50}$) is less than about 50 μm, or the $90^{th}$ volume percentile particle size ($D_{90}$) is less than about 80 μm, or any combination thereof.

The starting material, phosphonium bromide compound of Formula-IV, can be prepared from alcoholic compound of Formula (VI)

(VI)

The alcoholic compound of Formula (VI) is converted o phosphonium compound of Formula (IV) via formation of 3-(bromomethyl)-2-cyclopropyl-4(4'-flourophenyl)quinoline of Formula (V) by the known process reported in the prior art. WO 95/11898 A1 in its reference example-7 and Example-1 or as per the process disclosed in U.S. Pat. No. 6,627,636 and U.S. Pat. No. 5,763,675.

(V)

The bromo compound of Formula (V) 3-(bromomethyl)-2-cyclopropyl-4-(4'-flourophenyl)quinoline with wittig reagent like triphenyl phosphine in suitable non-polar solvents like toluene, o-xylene, chlorobenzene etc to obtain phosphonium bromide compound of Formula (IV).

The starting reagent, alcohol compound of Formula (VI) can be prepared from the known process reported in the art like *Tetrahedron Letters*, Vol. 34, No. 51, p.p. 8271-8274 (1993); *Heterocycles*, Vol. 50, No. 1, 1999; *Drugs of Future* 1998 23 (8) or *Tetrahedron Asymmetry* 1993, Vol. 4, pp. 201-204 are reported herein as reference in its entirety.

As set forth in the following schemes, the process of the invention for the preparation of Febuxostat involves the following chemical reactions.

The crystalline form of pitavastatin calcium can be characterized by PXRD, DSC, and IR as follows:
(a) Characterization by PXRD The X-ray powder diffraction spectrum was measured under the following experimental conditions:
Instrument: X-Ray Diffractometer, D/Max-2200/PC Make: Rigaku, Japan.
X-Ray: Cu/40 kv/40 mA
Diverging: 1°
Scattering Slit: 1°
Receiving Slit: 0.15 mm
Monochromator RS: 0.8 mm
Counter: Scintillation Counter
Scan Mode: Continuous
Scan Speed: 3.000°/Min
Sampling Width: 0.020
Scan Axes: Two Theta/Theta
Scan Range: 2.000° to 40.000°
Theta Offset: 0.000°

(b) Characterization by Differential Scanning Calorimetry (DSC)
Analytical Method:

Differential scanning calorimetric analysis was performed using a Perkin Elmer Diamond DSC control unit and a DSC 300° C. differential scanning calorimeter. 2-5 mg samples were placed in crimped aluminum pans and heated from 50° C. to 250° C. in a liquid nitrogen atmosphere at a heating rate of 10° C./minute. Zinc-Indium was used as the standard substance.

(c) The IR spectrum was measured by the KBr method.

The Examples are set forth to aid in understanding the invention but are not intended to, and should not be construed to; limit its scope in any way. The examples do not include detailed descriptions of conventional methods. Such methods are well known to those of ordinary skill in the art and are described in numerous publications.

Preparation-1:

Preparation of 3-(bromomethyl)-2-cyclopropyl-4-(4'-flourophenyl)quinoline (V)

1 Kg of alcohol compound of Formula (VI) and 8 L of methylene dichloride were taken in reactor at 0° C. 0.462 Kg of freshly prepared phosphonium bromide solution in 2 L methylene dichloride was added slowly and stirred at 25° C. for 2 hours. After the completion of the reaction as monitored by TLC, the reaction mixture was quenched with 5% sodium bicarbonate solution to adjust the pH from 7-8. The organic layer was separated and washed with 5 L water followed by removal of solvent under vacuum at 45° C. The residue was treated with 2.5 L heptane at 60° C. and cooled to 15° C. The product was filtered at 15° C. and dried under vacuum at 55° C. for 8 hours to obtain 3-(bromomethyl)-2-cyclopropyl-4-(4'-flourophenyl)quinoline.

Preparation-2:

Preparation of Phosphonium Bromide Compound of Formula (IV)

with toluene. The product was dried in tray dryer at 55° C. for 8 hours to obtain phosphonium bromide compound of Formula (IV).

Example-1

Preparation of (4R,6S)-(E)-6-[2-(2-cyclopropyl-4-(4-flourophenyl)quinoline-3-yl)-vinyl-2,2-dimethyl-1,3-dioxane-4-yl]acetic acid tertiary butyl ester compound of Formula II

1 Kg of 3-(bromomethyl)-2-cyclopropyl-4-(4'-flourophenyl)quinoline, 10 L of toluene and 300 mL of isopropanol were taken in reactor and heated at 50° C. 0.874 Kg of triphenyl phosphine solution in 2 L toluene was added slowly and stirred for 3 hours. The reaction mixture was cooled to 25° C. and stirred for 1 hour. The product was filtered and washed To a solution of 0.751 Kg of tert-butyl-2-((4R,6S)-6-formul-2,2-dimethyl-1,3-dioxan-4-yl)acetate (III) in 7 L of dimethylsulphoxide, was added 1 Kg of phosphonium bromide compound of Formula (IV) and 0.67 Kg of potassium carbonate. The reaction mixture was stirred at 25° C. for 10 hours under nitrogen atmosphere. The reaction mixture was quenched with water and extracted with toluene. The organic layer was concentrated and the compound of Formula (II) was isolated using isopropanol. The product thus obtained was recrystallized in methanol.

Example-2

Preparation of Pitavastatin Calcium of Formula (I)

To a solution of 100 g of (4R,6S)-(E)-6-[2-(2-cyclopropyl-4-(4-flourophenyl)quinoline-3-yl)-vinyl-2,2-dimethyl-1,3-dioxane-4-yl]acetic acid tertiary butyl ester compound of Formula II in 1 L methanol, was added 272.8 mL 1N HCl solution at 25° C. The reaction mixture was stirred for 8 hours. The reaction mixture was cooled to 15° C. and treated with 23.2 g 10% sodium hydroxide solution. The reaction mixture was stirred for 4 hours at 25° C. and quenched in water (preboiled). The reaction mass was treated with 92 mL 1 N HCl solution to adjust the pH to about 8.0 and treated with methylene dichloride for washing. The separated aqueous layer was treated with 100 g of calcium chloride hexahydrate and stirred for 30 min at 25° C. The solution was cooled to 15° C., filtered and washed with water. The product was dried in hot air oven for 12 hours to obtain 82 g of crystalline pitavastatin calcium having water content from about 8% to 12.0%. The wet-cake was dried under vacuum at 60 to 65° C. for 1-5 hours to get water content from about 2.0 to 4.0% w/w.

Example 3

Preparation of Crystalline Pitavastatin Calcium 10 g of crystalline pitavastatin calcium was dissolved in a mixture of 25 ml THF and 25 ml water. To this stirred solution, was slowly added 10 ml n-heptane at room temperature, and stirred for an additional 16 hours. The resulting suspension was filtered and dried in air. The obtained solid was crystalline form having water content more than 8%. The product was dried in hot air oven for about 12 hours under vacuum to obtain 8.2 g of crystalline pitavastatin calcium having water content of 3.0% having the X-ray diffraction pattern depicted in FIG. 1.

Example 4

Preparation of Crystalline Pitavastatin Calcium 10 g of pitavastatin calcium having water content 8% to 12% of example-2 was dried in a Fluid Bed Dryer at 45° C. for 2 days to obtain crystalline pitavastatin calcium having water content less than 3.5% wt/wt. An X-ray diffraction study on the product showed it to be crystalline (FIG. 1.)

Example 5

Preparation of Crystalline Pitavastatin Calcium 10 g of pitavastatin calcium having water content 8% to 12% was dried in a vacuum tray dryer at about 5 to about 60° C., under pressure of less than 30 mm/Hg for a period of 24 hours to obtain crystalline pitavastatin calcium having water content less than 5% wt/wt. An X-ray diffraction study on the product showed it to be crystalline (FIG. 1.)

Example 6

Packing of Crystalline Pitavastatin Calcium

The crystalline pitavastatin calcium obtained in example-2 having water content of about 3.1% was placed under nitrogen atmosphere in a double polythene bag or non-permeable bag tied with a thread, placing the above bag inside a black color polyethylene bag, optionally containing oxygen busters and sealing it, placing above the black color polyethylene inside a triple laminated bag optionally containing oxygen busters and sealing it, and placing the sealed triple laminated bag inside a closed high density polyethylene (HDPE) container, sealing it and storing in a controlled environment chamber from about 25° C. to about 40° C.

ADVANTAGES OF THE INVENTION

1. The present invention provides crystalline pitavastatin calcium having water content less than about 5% wt/wt.
2. The present invention provides storage stable crystalline pitavastatin calcium having water content less than about 5% wt/wt.
3. The present invention provides crystalline pitavastatin calcium having at least one or more of following impurities less than 0.15% by area percentage of HPLC. pitavastatin desflouro; pitavastatin diastereomer; pitavastatin 5-oxo; pitavastatin lactone; pitavastatin tert butyl diol ester; pitavastatin condensed; pitavastatin enantiomer or any other unknown single individual impurity.
4. The present invention also provides crystalline pitavastatin calcium substantially free from crystal Form A having a peak of relative intensity of more than 25% at a diffraction angle (2θ) of 30.16°.
5. The present invention provides stable pitavastatin calcium containing after exposure to a relative humidity of 75% at 40° for a period of at least three months.
6. The present invention provides stable pitavastatin calcium containing after exposure to a relative humidity of 60% at 25° for a period of at least three months.
7. The process provided is eco-friendly, economically viable and easily scalable on large scale production.

While the present invention has been described in terms of its specific embodiments, certain modifications and equivalents will be apparent to those skilled in the art and are intended to be included within the scope of the present invention.

We claim:

1. Storage stable pitavastatin calcium having a water content less than about 5% wt/wt and having characteristic X-ray powder diffraction peaks at 2-theta values of about 6.7°, 9.0°, 11.1°, 19.6°, and 21.0°±0.2°.

2. The stable pitavastatin calcium as claimed in claim 1, wherein the pitavastatin calcium has the X-ray powder diffraction pattern as shown in FIG. 1.

3. The stable pitavastatin calcium as claimed in claim 1, wherein the pitavastatin calcium is substantially free of crystal Form-A, wherein Crystal Form-A is characterized by having an X-ray powder diffraction peak having a relative intensity of more than 25% at a diffraction angle (2θ) of 30.16°.

4. The stable pitavastatin calcium as claimed in claim 1, wherein the pitavastatin calcium is substantially free of crystal Form-A of pitavastatin calcium characterized by the absence of an X-ray powder diffraction peak having a relative intensity of more than 25% at a diffraction angle (2θ) of 30.16°.

5. The stable pitavastatin calcium as claimed in claim 1, wherein the pitavastatin calcium is substantially free of crystal Form-A of pitavastatin calcium characterized by the absence of an X-ray powder diffraction peak having a relative intensity of more than 25% at a diffraction angle (2θ) of 30.16° after storage for 3 months at 40° C. and a relative humidity of 75%.

6. The stable pitavastatin calcium as claimed in claim 1, wherein the pitavastatin calcium is substantially free of crystal Form-A of pitavastatin calcium characterized by the absence of an X-ray powder diffraction peak having a relative intensity of more than 25% at a diffraction angle (2θ) of 30.16° after storage for 3 months at 25° C. and a relative humidity of 60%.

7. Stable crystalline pitavastatin calcium having characteristic X-ray powder diffraction peaks at 2-theta values of about 6.7°, 9.0°, 11.1°, 19.6°, and 21.0°±0.2°, which is substantially free of crystal Form-A of pitavastatin calcium, in which the absence of Form A pitavastatin calcium is characterized by the absence of and does not show a X-ray powder diffraction peak having a relative intensity of more than 25% at a diffraction angle (2θ) of 30.16°.

8. The stable pitavastatin calcium as claimed in claim 1, which is substantially pure.

9. A process for the preparation of a stable crystalline form of pitavastatin calcium according to claim 1, wherein the crystalline pitavastatin calcium has a water content of less than about 5% wt/wt and characteristic X-ray powder diffraction peaks at 2-theta values of about 6.7°, 9.0°, 11.1°, 19.6°, and 21.0°±0.2°, the process comprising:
a) obtaining a solution of pitavastatin calcium in one or more solvents; and
b) isolating the crystalline pitavastatin calcium optionally, in the presence of one or more anti-oxidants.

10. The process as claimed in claim 9, wherein the solvent comprises one or more of chlorinated hydrocarbons, alcohols, ketones, aliphatic or cyclic ethers, water, or mixtures thereof.

11. The process as claimed in claim 9, wherein the solvent comprises one or more of methylene dichloride, ethylene dichloride, chlorobenzene, methanol, ethanol, isopropanol, butanol, acetone, methylethyl ketone, diisopropyl ether, methyl tert-butyl ether, 1,4-dioxane, tetrahydrofuran and water, or mixtures thereof.

12. The process as claimed in claim 9, wherein the antioxidant comprises one or more of butylated hydroxy toluene (BHT), butylated hydroxy anisole (BHA), n-propyl gallant, L-ascorbic acid or a-tocopherol.

13. The process as claimed in claim 9, further comprising additional drying of the pitavastatin calcium obtained.

14. The process as claimed in claim 13, wherein the pitavastatin calcium is dried till water content is less than about 5% wt/wt.

15. The process as claimed in claim 13, further comprising packaging the pitavastatin calcium under controlled conditions.

16. A process for the preparation of pitavastatin calcium according to claim 1, wherein the crystalline pitavastatin calcium has a water content of less than about 5% wt/wt and characteristic X-ray powder diffraction peaks at 2-theta values of about 6.7°, 9.0°, 11.1°, 19.6°, and 21.0°±0.2°, the process comprising:
(a) providing the pitavastatin calcium in crystalline form having a water content in the range of 8% to 12%;
(b) contacting the pitavastatin calcium with humid air in a fluidized bed drier;
(c) maintaining the pitavastatin calcium at a temperature of from about 5 to about 60° C., under pressure of less than 30 mm/Hg for a period of from about 1 hour to about 5 days; and
(d) recovering the pitavastatin calcium in crystalline form having a water content less than about 5% wt/wt.

17. A process for stabilizing crystalline pitavastatin calcium according to claim 1, wherein the crystalline pitavastatin calcium has a water content of less than about 5% wt/wt and characteristic peaks in X-ray powder diffraction at about 6.7°, 9.0°, 11.1°, 19.6°, and 21.0°±0.2° (2θ), the process comprising:
(a) placing crystalline pitavastatin calcium under nitrogen atmosphere in a double polythene bag or non-permeable bag tied with a thread;
(b) placing the bag of step (a) inside a black color polyethylene bag, optionally containing oxygen busters and sealing it;
(c) placing the bag of step (b) inside a triple laminated bag, optionally containing oxygen busters and sealing it; and
(d) placing the sealed triple laminated bag inside a high density polyethylene (HDPE) container, sealing it and storing in a controlled environment chamber from about 25° C. to about 40° C.

18. A process for the preparation of stable pitavastatin calcium of Formula I according to claim 1, (I)

wherein the crystalline pitavastatin calcium has a water content of less than about 5% wt/wt and characteristic peaks in X-ray powder diffraction at about 6.7°, 9.0°, 11.1°, 19.6°, and 21.0°±0.2° (2θ), the process comprising:

(a) reacting the phosphonium bromide compound of Formula-IV (IV)

with an aldehyde compound of Formula-III (III)

in the presence of an alkali or alkaline earth metal bases in one or more of suitable solvents to provide an olefin compound of Formula-II;

(II)

(b) hydrolyzing the olefinic compound of Formula-II by subjecting under the acidic conditions to remove the acetonide and form diol compound, which upon treating with an alkali metal hydroxide base to form the corresponding alkali metal salt of pitavastatin (Ia);

(Ia)

(c) treating the alkali metal salt of pitavastatin (Ia) with a calcium source to obtain pitavastatin calcium (I);
(d) obtaining a solution of pitavastatin calcium in one or more solvents; and
(e) isolating the crystalline pitavastatin calcium optionally, in the presence of one or more anti-oxidants.

19. The process as claimed in claim 18, wherein the alkali or alkaline earth metal bases comprise of one or more of sodium hydroxide, potassium hydroxide, lithium hydroxide, potassium carbonate, sodium carbonate, lithium carbonate, and cesium carbonate.

20. The process as claimed in claim 18, wherein the suitable solvent in step (a) comprises one or more of dimethylformamide, dimethylsulfoxide, dimethylacetamide, tetrahydrofuran, N-methyl-pyrrolidone, or mixtures thereof.

21. The process as claimed in claim 18, wherein the suitable acid comprises one or more of hydrochloric acid, acetic acid, sulfuric acid, nitric acid, and phosphoric acid.

22. The process as claimed in claim 18, wherein the alkali metal hydroxide comprises one or more of sodium hydroxide, potassium hydroxide, and lithium hydroxide.

23. The process as claimed in claim 18, wherein the suitable calcium source comprises one or more of calcium chloride, calcium methoxide, calcium acetate and hydrates thereof.

24. The process as claimed in claim 18, wherein the solvent in step (d) comprises one or more of chlorinated hydrocarbons, alcohols, ketones, aliphatic or cyclic ethers, water, or mixtures thereof.

25. The process as claimed in claim 24, wherein the solvent comprises one or more of methylene dichloride, ethylene dichloride, chlorobenzene, methanol, ethanol, isopropanol, butanol, acetone, methylethyl ketone, diisopropyl ether, methyl tert-butyl ether, 1,4-dioxane, tetrahydrofuran and water, or mixtures thereof.

26. The process as claimed in claim 25, wherein the antioxidant comprises one or more of butylated hydroxy toluene (BHT), butylated hydroxy anisole (BHA), n-propyl gallant, L-ascorbic acid or a-tocopherol.

27. A pharmaceutical composition comprising a therapeutically effective amount of crystalline pitavastatin calcium having characteristic X-ray powder diffraction peaks at 2-theta values of about 6.7°, 9.0°, 11.1°, 19.6°, and 21.0°±0.2° and a water content of less than about 5%, and one or more pharmaceutically acceptable carriers, excipients or diluents.

28. A pharmaceutical composition comprising a therapeutically effective amount of crystalline pitavastatin calcium having characteristic X-ray powder diffraction peaks at 2-theta values of about 6.7°, 9.0°, 11.1°, 19.6°, and 21.0°±0.2° and a water content of less than about 5% and substantially free from one or more of its corresponding impurities as measured by HPLC.

29. A pharmaceutical composition comprising crystalline pitavastatin calcium having characteristic X-ray powder diffraction peaks at 2-theta values of about 6.7°, 9.0°, 11.1°, 19.6°, and 21.0°±0.2°, a water content of less than 5%, and being substantially free of crystal Form A of pitavastatin calcium characterized by having a peak of relative intensity of more than 25% at a diffraction angle (2θ) of 30.16°.

30. Crystalline pitavastatin calcium characterized by X-ray powder diffraction peaks at about 6.7°, 9.0°, 11.1°, 19.6°, 21.0°±0.2° (2θ) having a particle size distribution wherein the $10^{th}$ volume percentile particle size ($D_{10}$) is less than about 20 μm, the $50^{th}$ volume percentile particle size ($D_{50}$) is less than about 50 μm, or the $90^{th}$ volume percentile particle size ($D_{90}$) is less than about 80 μm, or any combination thereof.

31. The stable pitavastatin calcium as claimed in claim 8, wherein the substantially pure pitavastatin calcium contains less than about 0.15% (wt/wt) of any single impurity.

32. The stable pitavastatin calcium as claimed in claim 8, wherein the substantially pure pitavastatin calcium contains less than about 0.3% (wt/wt) of any pitavastatin diastereomeric impurity and pitavastatin enantiomeric impurity.

\* \* \* \* \*